US010650667B1

(12) United States Patent
Afghah et al.

(10) Patent No.: US 10,650,667 B1
(45) Date of Patent: May 12, 2020

(54) FALSE ALARM REDUCTION SYSTEMS AND RELATED METHODS

(71) Applicants: Arizona Board of Regents acting for and on behalf of Northern Arizona University, Flagstaff, AZ (US); The Regents of the University of Michigan, Ann Arbor, MI (US)

(72) Inventors: Fatemeh Afghah, Flagstaff, AZ (US); Abolfazl Razi, Flagstaff, AZ (US); Kayvan Najarian, Flagstaff, AZ (US); Sayedmohammadreza Soroushmehr, Flagstaff, AZ (US)

(73) Assignees: Arizona Board of Regents acting for and on behalf of Northern Arizona University, Flagstaff, MI (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/195,585

(22) Filed: Nov. 19, 2018

Related U.S. Application Data

(60) Provisional application No. 62/588,309, filed on Nov. 17, 2017.

(51) Int. Cl.
*G08B 29/00* (2006.01)
*G08B 29/18* (2006.01)
*G08B 21/04* (2006.01)
*A61B 5/00* (2006.01)
*A61B 5/145* (2006.01)
(Continued)

(52) U.S. Cl.
CPC .......... *G08B 29/185* (2013.01); *A61B 5/0022* (2013.01); *A61B 5/021* (2013.01); *A61B 5/046* (2013.01); *A61B 5/0464* (2013.01); *A61B 5/14542* (2013.01); *A61B 5/746* (2013.01); *G08B 21/0453* (2013.01)

(58) Field of Classification Search
CPC .............. G08B 29/185; G08B 21/0453; A61B 5/0022; A61B 5/021; A61B 5/0464; A61B 5/14542; A61B 5/746
USPC .......................................................... 340/506
See application file for complete search history.

(56) References Cited

U.S. PATENT DOCUMENTS 6,272,479 B1 * 8/2001 Farry ....................... A61N 1/08
700/213
2010/0082513 A1 * 4/2010 Liu ..................... H04L 63/1458
706/46

(Continued)

*Primary Examiner* — Naomi J Small
(74) *Attorney, Agent, or Firm* — Adam R. Stephenson, Ltd.

(57) ABSTRACT

Implementations of a system for determining the relevancy of a plurality of alarms may include: a plurality of sensors configured to be coupled to a patient, wherein the plurality of sensors is configured to gather physiological data, a medical monitoring device coupled to the plurality of sensors through a telecommunication channel, and wherein the medical monitoring device is configured to determine a physiological state of the patient using the physiological data. The medical monitoring device may be further configured to issue a plurality of alarm states, and a processing unit coupled to the medical monitoring device through a telecommunication channel, is then configured to evaluate the plurality of alarm states, determine the relevancy of each alarm state of the plurality of alarm states, and issue one or more alarms corresponding with each relevant alarm state to a computing device associated with a user.

18 Claims, 3 Drawing Sheets

(51) Int. Cl.
*A61B 5/021* (2006.01)
*A61B 5/0464* (2006.01)
*A61B 5/046* (2006.01)

(56) References Cited

U.S. PATENT DOCUMENTS

| | | | |
|---|---|---|---|
| 2015/0150086 A1* | 5/2015 | Clark | G16H 10/60 726/3 |
| 2015/0186608 A1* | 7/2015 | Fuller | G08B 21/02 705/2 |
| 2016/0093205 A1* | 3/2016 | Boyer | A61B 5/02416 340/506 |

* cited by examiner

FALSE ALARM REDUCTION SYSTEMS AND RELATED METHODS

CROSS REFERENCE TO RELATED APPLICATIONS

This document claims the benefit of the filing date of U.S. Provisional Patent Application 62/588,309, entitled "Computational Framework Utilizing Coalition Game Theory for False Alarm Reduction" to Afghah, et al. which was filed on Nov. 17, 2017, the disclosure of which is hereby incorporated entirely herein by reference.

GOVERNMENT LICENSE RIGHTS

The subject matter in this application was made with government support under Award Number 1657260 awarded by the National Science Foundation. The government has certain rights in the invention.

BACKGROUND

1. Technical Field

Aspects of this document relate generally to medical device systems and methods.

2. Background

Medical monitoring is often carried out using various systems with sensors used to collect data from a patient. Various medical monitoring equipment uses sensor types that couple directly to the patient's skin or monitor systems attached to the patient (like ventilators). A wide variety of data is collected by medical monitoring systems relating to the condition of the patient and/or the equipment attached to the patient.

SUMMARY

Implementations of a system for determining the relevancy of a plurality of alarms may include: a plurality of sensors configured to be coupled to a patient, wherein the plurality of sensors is configured to gather physiological data, a medical monitoring device coupled to the plurality of sensors through a telecommunication channel, and wherein the medical monitoring device is configured to determine a physiological state of the patient using the physiological data. The medical monitoring device may be further configured to issue a plurality of alarm states, and a processing unit coupled to the medical monitoring device through a telecommunication channel, is then configured to evaluate the plurality of alarm states, determine the relevancy of each alarm state of the plurality of alarm states, and issue one or more alarms corresponding with each relevant alarm state to a computing device associated with a user.

Implementations of a system for determining the relevancy of a plurality of alarms may include one, all, or any of the following:

The physiological data may include electrocardiographic data, arterial blood pressure data, plethysmographic data, or any combination thereof.

The sensors may include an electrocardiogram sensor, an arterial blood pressure sensor, or a pulse oximeter.

The plurality of alarm states may include an alarm for asystole, an alarm for bradycardia, an alarm for tachycardia, an alarm for ventricular tachycardia, an alarm for ventricular fibrillation, or any combination thereof.

The relevancy of the one or more alarm states may be a true state or a false state.

The processing unit may further be configured to choose a plurality of top informative alarms using a Banzhaf power and the processing unit. The processing unit may classify one or more chosen top informative alarms from the plurality of top informative alarms into false alarms and true alarms using a Bayes-Net classifier.

The Banzhaf power may be defined as:

$$n_i(v) = \frac{1}{2^{n-1}} \sum_{S \subset N_1} \varsigma_i^S, \text{ wherein } \frac{1}{2^{n-1}}$$

represents the fraction of times that an alarm state from among the plurality of alarm states has a critical role, and $\Sigma_{S \subset N_1} \xi_i^S$ represents the impact of an alarm state from among the plurality of alarm states on each other alarm state ($F_i$) from among the plurality of alarm states where $$\zeta_i = \begin{cases} 1, & I(S; C \mid F_i) \geq 0, \gamma_i^S \geq \frac{|S|}{2} \\ 0, & \text{otherwise} \end{cases}.$$

The medical monitoring device may include a translating component configured to convert each of a plurality of physiological signals from each of the plurality of sensors.

Implementations of a method for determining the relevancy of a plurality of alarms may include: gathering physiological data using a plurality of sensors, wherein the plurality of sensors is configured to be coupled to a patient, and determining a physiological state of the patient using the physiological data, using a medical monitoring device coupled to the plurality of sensors through a telecommunication channel. The method may further include, using the medical monitoring device, issuing a plurality of alarm states, evaluating the plurality of alarm states using a processing unit, determining the relevancy of each alarm state of the plurality of alarm states using the processing unit, and issuing one or more alarms corresponding with each relevant alarm state to a computing device associated with a user.

Implementations of a method for determining the relevancy of a plurality of alarms may include one, all, or any of the following:

Issuing one or more alarms may include issuing the one or more alarms to the computing device only after the relevancy of each alarm state from among the plurality of alarm states is determined to be true.

Determining the physiological state of the patient may include translating each of a plurality of physiological signals from each of the plurality of sensors using a translating component on the medical monitoring device.

Determining the relevancy of each alarm state of the plurality of alarm states may include choosing a plurality of top informative alarms from among the plurality of alarm states using a Banzhaf power and the processing unit.

Choosing the plurality of top informative alarms from among the plurality of alarm states using the Banzhaf power may include using the Banzhaf power defined as:

$$n_i(v) = \frac{1}{2^{n-1}} \sum_{S \subset N_1} \varsigma_i^S,$$

wherein $$\frac{1}{2^{n-1}}$$

represents the fraction of times that an alarm state from among the plurality of alarm states has a critical role, and $\Sigma_{S \subset N_1} \xi_i^S$ represents the impact of an alarm state from among the plurality of alarm states on each other alarm state ($F_i$) from among the plurality of alarm states where $$\zeta_i = \begin{cases} 1, & I(S; C \mid F_i) \geq 0, \gamma_i^S \geq \frac{|S|}{2} \\ 0, & \text{otherwise} \end{cases}.$$

Determining the relevancy of each alarm state of the plurality of alarm states may include classifying one or more chosen top informative alarms from a plurality of top informative alarms of the plurality of alarm states into false alarms and true alarms using a Bayes-Net classifier using the processing unit.

Issuing one or more alarms corresponding with each relevant alarm state may includes issuing an alarm to a desktop computing device or mobile computing device.

Issuing a plurality of alarm states may include issuing an alarm for asystole, an alarm for bradycardia, an alarm for tachycardia, an alarm for ventricular tachycardia, an alarm for ventricular fibrillation, or any combination thereof.

Implementations of a method for issuing an alarm regarding a physiological state of a patient may include: receiving a plurality of alarm states from a medical monitoring device at a processing unit through a telecommunication channel and choosing a plurality of top informative alarms using a Banzhaf power and the processing unit. The method may further include classifying a one or more chosen top informative alarms from the plurality of top informative alarms into false alarms and true alarms using a Bayes-Net classifier using the processing unit, and issuing at least one alarm to a computing device associated with a user if any one or more chosen top informative alarms is classified as true.

Implementations of a method for issuing an alarm regarding a physiological state of a patient may include one, all, or any of the following:

The method may include calculating interdependencies of the plurality of top informative alarms using the processing unit.

The method may include choosing the plurality of top informative alarms using the Banzhaf power including using the Banzhaf power defined as $$n_i(v) = \frac{1}{2^{n-1}} \sum_{S \subset N_1} \varsigma_i^S,$$

wherein $$\frac{1}{2^{n-1}}$$

represents the traction of times that an alarm state from among the plurality of alarm states has a critical role, and $\Sigma_{S \subset N_1} \xi_i^S$ represents the impact of an alarm state from among the plurality of alarm states on each other alarm state ($F_i$) from among the plurality of alarm states where $$\zeta_i = \begin{cases} 1, & I(S; C \mid F_i) \geq 0, \gamma_i^S \geq \frac{|S|}{2} \\ 0, & \text{otherwise} \end{cases}.$$

Choosing the plurality of top informative alarms may include determining a most informative subset of alarm states from among the plurality of alarm states, wherein determining may include establishing a relevance of the subset of alarm states to a target user and determining an interdependence among the subset of alarm states.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended false alarm reduction systems and related methods will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such false alarm reduction systems, and implementing components and methods, consistent with the intended operation and methods.

False alarms are widely considered a major hazard in medical technology. Alarm safety has also been determined as a national patient safety goal. The caregivers of patients can be overwhelmed with many alarm conditions per patient per day, of which many of these clinical alarms are meaningless or false.

False alarms can be due to several factors such as patient movement, noise, motion artifacts, missing data, malfunction of individual sensors, and imperfections in the patient-equipment contact. The amount of false alarms can result in many problems such as alarm fatigue among caregivers. This may also lead to caregivers' insensitivity to these unreliable alarms and increases the possibility of missing a true life-threatening event, as it could be lost in a cacophony of the noise of multiple alarms.

Additionally, the false alarms can result in care disruption, sleep deprivation, patient anxiety, inferior sleep structure, and depressed immune systems. The alarms in Intensive Care Units are mostly based on the measurements made by the individual machines/monitors, and majority of the alarms produced by these individual machines are generally considered false when reviewed by medical professionals. Accurate and reliable detection of false alarms can significantly limited by the complexity of patterns associated with critical alarms, the high level of noise affecting these patterns, and lack of integration of correlation among the collected signals from different sensors. One of the challenges of improving accuracy of false alarm detection is integrating multiple signals simultaneously collected from different devices and providing patient-centric decision-making mechanisms implementing a multi-parameter analysis to include all the input data while assisting the caregivers with identifying the real or true alarms.

Coalition game theory is utilized in the present implementation to improve the performance of feature selection by considering the contribution of the features on classification accuracy when the features are grouped with other features in the data set. Unlike non-cooperative game theory in which the features act individually, coalition game theory refers to a class of game theoretical approaches that applies the set of joint actions taken by a group of features.

In various system and method implementations, coalition game theory is utilized to process and evaluate data in a range of different applications including, by non-limiting example, medical clinical studies, gene expression, social media analytics, marketing, and climate observations, among other fields. The method implementations disclosed herein can be capable of identifying hidden correlations and dependencies in data sets to identify the most informative correlations using various predictors.

In various system and method implementations, a coalition-based game theoretic approach is utilized to decompose the collected signals in multiple resolutions, filter noise, and extract a set of additional geometric features describing the signal using a transformation. The system and method implementations then consider non-linear correlations and mutual information among the features collected from various devices to determine salient predictors of false alarms resulting in significantly improved prediction accuracy.

A coalition-theoretical model based on the Banzhaf power index that accounts for the interdependency among the extracted features and their relevancy to the target class is disclosed in this document. The Banzhaf power index metric is proportional to the number of times that a feature is a critical player for a coalition. The information-theoretic notion for the Banzhaf power is such that a feature is determined to have a critical impact on a set of features if it increases the relevancy of the selected feature set on a target class and is also interdependent on more than half of them members in the set. The results using the Banzhaf power index used in this way may validate the desirable performance improvement of system and method implementations' ability to reduce the false alarm rate.

In various implementations, relevant features are extracted from the entire time-series signals to detect the false alarms, because if the original signals were considered in their entirety, this would result in a large number of highly correlated features compared to the sample size that would greatly increase the chance of over-fitting the model to the training data. The resulting over-fit model then would be unable to accurately process new, previously-untrained data in real life operation.

In various implementations, discrete wavelet transforms (DWT) are applied on the 1-D input signals of various physiological sensors (the time series data received from a sensor). Some non-limiting examples of data from these sensors may include electrocardiographic data, arterial blood pressure data, plethysmographic data, any combination thereof, or any other type of physiological sensor data type. Various physiological states indicated by physiological data associated with a patient could include asystole, meaning there is no heartbeat for a least 4 second; extreme bradycardia, meaning the heart rate is less than 40 beats per minute for 5 consecutive beats; extreme tachycardia, meaning the heart rate is higher than 140 beats per minute; ventricular tachycardia, meaning there are at least 5 ventricular beats with a heart rate higher than 100 beats per minute; ventricular flutter/fibrillation, meaning there is a fibrillatory flutter, or oscillatory waveform for at least 4 seconds; or any other physiological state indicator. In various implementations, details in signals are separated, compared to other transforms, and then used to eliminate the noise with a low distortion rate.

In various system and method implementations, a set of wavelets (like DWT wavelets) defines a filter bank which can be used for signal component analysis and the resulting wavelet transform coefficients can be further applied as signal features for classification. DWT components are shifted and scaled versions of the mother wavelet defined as:

$$\psi_{i,j}(t) = 1/\sqrt{2^i}\,\psi\left(\frac{t-j\times 2^i}{2^i}\right)$$

where i, j are scale and shift parameters. A Daubechies wavelet of class D-2N may be employed in various implementations where $\psi(t)=\sqrt{2}\Sigma_k(-1)^k h_{2N-1-k}\times\emptyset(2-1)$. and: $\emptyset(t)=\sqrt{2}\Sigma_k h_k\times\emptyset(2t-k)$, where h shows a high-pass filter. At each level of decomposition process, DWT decomposes the signals into approximate and detail coefficients. Approximation set is obtained by applying a high-pass filter at low scales and detail coefficients are computed by applying a low-pass filter at high scales. Daubechies 8 for electrocardiogram (ECG) signal is used, as there is a good match between the shape of an ECG signal and this wavelet. Daubechies 4 is used for plethysmograph (PLETH) and arterial blood pressure (ABP) signals for the same reason. Additional disclosure on methods and systems for using DWTs as a filter bank for feature extraction may be found in the paper by Prochazka et al., entitled "Wavelet transform use for feature extraction and EEG signal segments classification," 2008 3rd International Symposium on Communications, Control and Signal Processing (IEEE, 2008) the disclosure of which is hereby incorporated entirely herein by reference In various implementations, wavelet coefficients may be calculated by convolving the high-pass filter, h and the corresponding low-pass filter, $g_k=h_{2N-1-k}$, with a signal and results are down-sampling the results. The calculated coefficients may be shown as $X=[E_1, \ldots, E_l, A_1, \ldots, A_l, P_1, \ldots, P_l]$, where Z shows the number of decomposition levels and 1 (L)=6. $E_i$, $A_i$, and Pi, respectively show the wavelet coefficients of ECG, ABP, and PLETH signals. For i=1, each of these parameters represents the detail coefficients and for i≠1 (L) each of them represents the approximate coefficient. The approximate and detail coefficients may be respectively calculated from $a_i(t)=\Sigma_k a_{i-1}(t)h_{2t-k}$ and $d_i(t)=\Sigma_k a_{i-1}(t)g_{2t-k}$ where $a_{i-1}$ shows the input signal (ECG, ABP, PLETH, etc.)

Table 1 illustrates various information-theoretic properties of wavelet vectors. In calculating various of these information-theoretic properties, the coefficients may be discretized using quantization levels obtained from Lloyd's algorithm and used an empirical distribution is used as an estimate for the unknown actual probability distribution from which the coefficients are derived.

TABLE 1

| No. | Feature |
|---|---|
| 1 | Mean |
| 2 | Mode |
| 3 | Median |
| 4 | Max |
| 5 | Min |
| 6 | Range |
| 7 | Variance |
| 8 | STD (σ) |
| 9 | $\mu_3$ |
| 10 | $\mu_4$ |
| 11 | Coeff. of var. |
| 12 | Kurtosis $\kappa(X) = \dfrac{\mu_4(X)}{\sigma_4(X)}$ |
| 13 | Skewness $\lambda(X) = \dfrac{\mu^3(X)}{\sigma^3(X)}$ |
| 14 | H mean $\dfrac{N}{\sum_{i=1}^{N} 1/X_i}$ |
| 15 | Interquartile range |
| 16 | Shannon entropy $H(X^2) = -\sum_{i=1}^{N} X_i^2 \log_2 X_i^2$ |
| 17 | Log energy $\sum_i \log X_i^2$ |
| 18 | $n_T(\max\{X_i\}/2)$ |
| 19 | $n_T(\sqrt{\Sigma X_i^2})$ |
| 20 | $n_T(5\sqrt{\Sigma X_i^2})$ |

Features 1-10 of Table 1 are typical statistical properties of the signal, where $\mu_n$ is the nth standardized sample moment calculated using $$\mu_n = \frac{\sum_{i=1}^{N}(X_i - \overline{X})^n}{N},$$

where $$\overline{X} = \frac{\sum_{i=1}^{N}(X_i)}{N}$$

in which $X_1, \ldots, X_N$ are the Nth wavelet coefficients associated with each signal probe. Kurtosis measures the peakedness of distribution and is defined as a ratio of the fourth standardized moment to the square of the variance. Skewness is a measure of the symmetry of distribution around zero. Harmonic mean is H mean in Table 1. Shannon entropy is an information theoretic property of the square of coefficients approximated by their sample counterparts. Finally, $n_T(\alpha)$ counts the number of times that the value of wavelet coefficients exceed the threshold $\alpha$, and is defined as:

$$n_T(\alpha) = \sum_{i=1}^{N} 1(|X_i|) > \alpha).$$

1(.) shows the indicator function. These features collectively capture the properties of the signal at different decomposition levels and may be used as input for the proposed feature selection method, in various implementations.

Various method and system implementations in this document employ a coalition game. A coalition game refers to a class of game theoretical approaches that study the set of joint actions taken by a group of players. The outcome of a coalition game is defined by how players can form coalitions and how the coalition payoff can be divided among its members.

Mathematically, a coalition game implementation can be defined with a pair of (N, v), where $N=\{F_1, F_2, \ldots, F_n\}$ is the set of players with cardinality of n (i.e., |N|=n). The characteristic function, v, is a real-valued function defined on the set of all coalitions, v: $2^N \to R$ and represents the total payoff that can be gained by the members of this coalition. The transferable utility coalition (TU-coalition) game is used for which the characteristic function satisfies the following conditions: 1) characteristic function of an empty coalition ¢ is zero (v(Φ)=O); 2) for two disjoint coalitions $S_i$ and $S_j$, ($S_i$, $S_j \subseteq N$), the characteristic function of their union has super-additivity property, meaning that $v(S_i \cup S_j) \geq v(S_j)$.

In the present feature selection method, the importance of the features is measured using the Banzhaf power. To define this metric, the concept of a simple game is first introduced. A simple game refers to a class of coalition games with characteristic function satisfying the following conditions: 1) $v(S) \in \{O, 1\}$, For all $S \subset N$; 2) $v(\Phi)=0$, $v(N)=1$; and 3) For S, $T \subset N$, if $S \subset T$, then $V(S) \leq v(T)$ (monotonicity).

Based on the first property, the coalitions are divided into two sets of winning coalitions, $W(v)=\{S \subset N | v(S)=1\}$ and losing coalitions defined as $L(v)=\{S \subset N | v(S)=O\}$. In these games, a player $F_i$ is called a swinger if the removal of this player from a winning coalition S converts it to a losing coalition, meaning that $V(S)=1$ and $v(S\setminus\{F_i\})=0$.

The Banzhaf power for player $F_i$, $\beta_i(v)$ represents the fraction of times that player has a critical role in converting a losing coalition to a winning one. Additional information regarding the Banzhaf power may be found in the article by John F. Banzhaf III, "Weighted Voting Doesn't Work: A Mathematical Analysis," *Rutgers Law Review* V. 19, No. 2 (1965, p. 317-343, the disclosure of which is hereby incorporated entirely herein by reference. The Banzhaf power is the expectation of player $F_i$ to be a swinger in a simple game model assuming that formation of all coalitions are equally probable, and is defined as:

$$\beta_i(v) = \frac{n_i(v)}{2^{n-1}},$$

where $n_i(v)$ counts all coalitions for which the player $F_i$ is a swinger (i.e., $\{S: S \subset N\setminus\{F_i\}, v(S \cup \{F_i\}) - v(S) = 1\}$). In the coalition-based feature selection method, the features are considered as the players of the game, and the characteristic function of a coalition, $v$, is measured by contribution of its members (features) to the performance of the classifier. The contribution of each feature is measured in the game noting all possible coalitions of the players using Banzhaf power. In various implementations, the criterion to determine the most informative subset of features is the relevance of this set to the target class as well as the interdependence among the group members. As non-limiting example, if the relevance of the feature $F_i$ on target class C, $R(F_i; C)$ is defined by their mutual information, $R(F_i; C) = I(F_i; C)$, the relevance of coalition S on target class C can be approximated as $$R(S; C) \cong \frac{1}{|S|} \sum_{F_j \in S} [I(F_j; C)].$$

Likewise, the change of relevance of a coalition S on target class C due to the knowledge of feature $F_i$, $(F_iS)$ is approximately $$I(S; C \mid F_i) \cong \frac{1}{|S|} \sum_{F_j \in S} [I(F_j; C \mid F_i) - I(F_j; C)].$$

Moreover, two features $F_i$ and $F_j$ may be defined to be interdependent of each other if the relevance between $F_j$ and the target class C is increased when $F_i$ ($I(F_j; C|F_i) > I(F_j; C)$), meaning that the impact of this feature cannot be overlooked in the model. Parameter $\gamma^1$s is defined to count the number of features in coalition S that are interdependent on feature $F_i$ as follows $\gamma_i^S = 1(I(F_j; C|F_i) > I(F_j; C))$, for all $F_j \in S$ where $1(.)$ is the indicator function.

In order to select the most informative subset of features, the impact of feature $F_i$ is determined on all possible coalitions of features excluding $F_i$, $\{S: S \subset N, F_i S\}$. Feature $F_i$ is a swinger for coalition S, if it increases the relevance of this coalition on the target class and also if it is interdependent with at least half of the members of coalition S. Then, a swinger index $\zeta i$ for feature $F_i$ is defined as:

$$\zeta_i = \begin{cases} 1, & I(S; C \mid F_i) \geq 0, \gamma_i^S \geq \frac{|S|}{2} \\ 0, & \text{otherwise} \end{cases}$$

Consequently, the Banzhaf power of feature $F_i$ calculates the ratio of all coalitions for which feature $F_i$ is a swinger. This parameter quantifies the power of features in turning the losing coalitions into winning ones and hence can be used to choose the top informative features, and can be defined as:

$$n_i(v) = \frac{1}{2^{n-1}} \sum_{S \subset N_1} \zeta_i^S,$$

wherein $$\frac{1}{2^{n-1}}$$

represents the fraction of times that an alarm state from among the plurality of alarm states has a critical role and $\Sigma_{S \subset N_1} \zeta_i^S$ represents the impact of an alarm state from among the plurality of alarm states on each other alarm state from among the plurality of alarm states.

Figure 1:
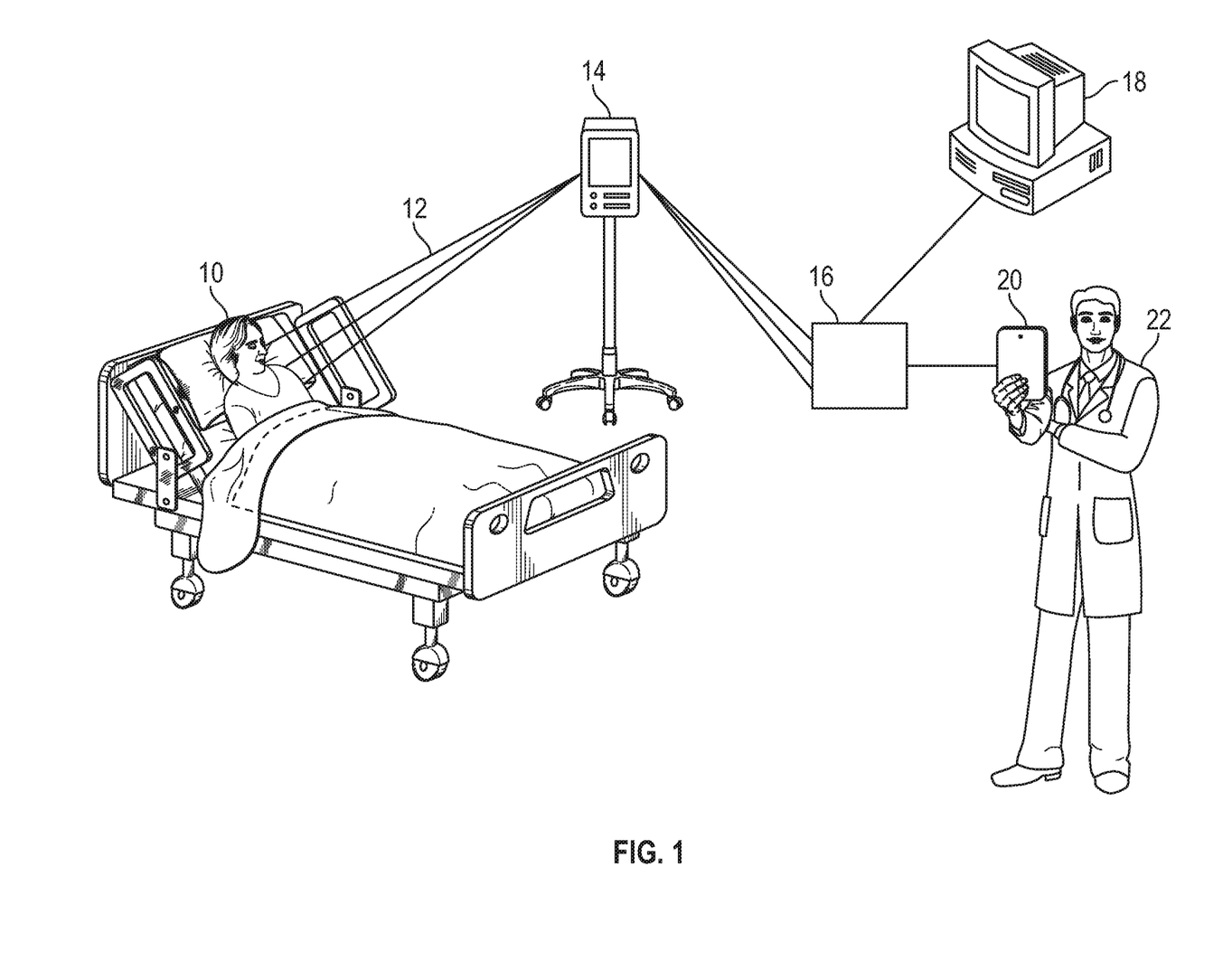
FIG. 1 illustrates an implementation of a system for determining the relevancy of a plurality of alarms.

Referring to FIG. 1, an implementation of a system for determining the relevancy of a plurality of alarms is illustrated. In various implementations, physiological sensors 12 are coupled to a patient 10. In various implementations, the sensors 12 may be coupled to the patient 10 in any way that allows for the detection, sensing, calculation, or monitoring of any of the patient's 10 detectable health, physiological, chemical, or biomedical data. The outputs of the physiological sensors 12 are coupled to one or more medical monitoring device(s) 14, where the physiological data of the patient 10 is received, and may also be stored and/or processed. The outputs of the physiological sensors 12 can be coupled to the medical monitoring device 14 by, as non-limiting example, wired or wireless telecommunication channels. Output from the medical monitoring device 14 is then sent to, and received by, a processing unit 16 as input. The output from the medical monitoring device 14 may be, in some non-limiting examples, be transmitted to the processing unit 16 by wired or wireless telecommunication channels. In various implementations, this output can include, by non-limiting example, raw physiological data; raw physiological signals; raw physiological indicators; processed physiological data; processed physiological signals; processed physiological indicators; one or more alarms based on any of the raw and/or processed data, signals, indicators; or any combination thereof.

The processing unit 16 then evaluates, processes, makes a determination, or classifies, the input it receives from the medical monitoring device 14. In various implementations, the evaluation, processing, determining, and/or classification is carried out using a method employing a coaling game like any disclosed in this document. Once the processing unit 16 completes the evaluation, process, determination, or classification, it then sends its output in the form of, by non-limiting example, one or more alarms, alerts, or signals to a computing device associated with a user. In various implementations, the computing device may be a desktop computing device 18, a mobile computing device 20, associated with one or more users 22, such as a medical professional, in some non-limiting examples. Examples of mobile computing devices that may be utilized in various implementations may include, by non-limiting example, tablets, laptops, smartphones, cell phones, thin clients, and any other movable computing device.

Various system implementations are used to take the large number of alarms and alerts generated by the medical monitoring device 14 and improve the function of the medical monitoring devices and the entire system by allowing the system to determine what alarms and alerts are actually true, meaning they actually require intervention/involvement of medical personnel and those which are false, meaning they do not need attention or intervention. By only transmitting those alarms, alerts, or signals that correspond to true alarms/alerts, the system significantly improves its ability to alert medical professionals by ensuring alarm fatigue does not prevent the professionals' ability to respond to true alarms. To accomplish this, the processing unit 16 uses various implementations of a method of determining the relevancy of a plurality of alarms. While the particular system implementation illustrated in FIG. 1 relates to a medical system that uses medical alarms, in various implementations, virtually any other process that employs sensor data to generate alarm conditions could utilize a processing unit and the various methods disclosed herein to determine those alarms that are true and pass them to operating personnel. Examples of processes where system and method implementations could be used include chemical processing plants, manufacturing process equipment, manufacturing processing lines, power generation systems, computerized control systems, and any other system where sensor data is turned to alarms and the alarms benefit from a secondary processing to determine which alarms are true and which are false.

Figure 2:
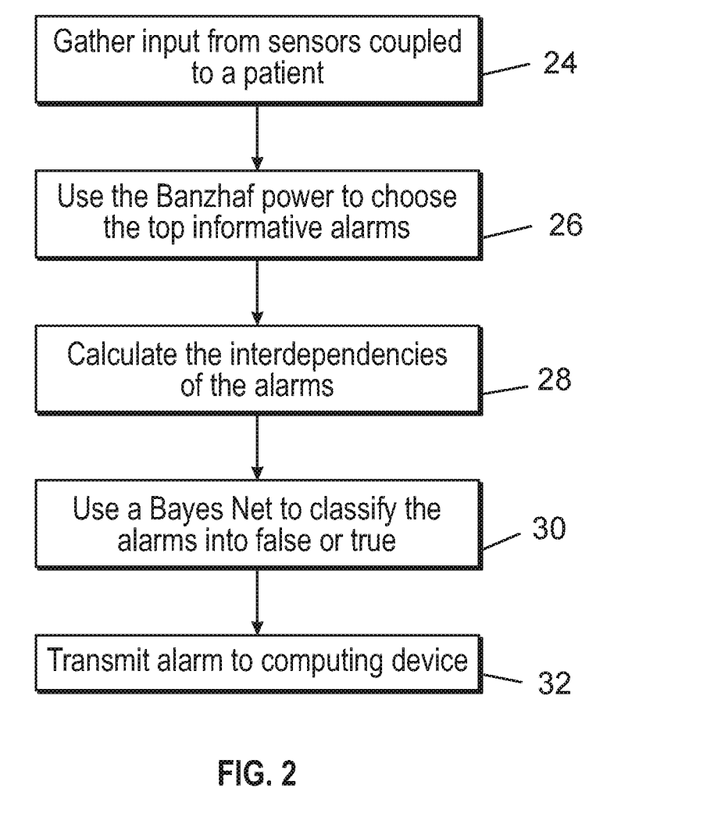
FIG. 2 is a flow diagram of an implementation of a method of determining the relevancy of a plurality of alarms and issuing an alarm regarding a physiological state of a patient.

Referring to FIG. 2, a flow diagram of an implementation of a method of determining the relevancy of a plurality of alarms and issuing an alarm regarding a physiological state of a patient is illustrated. First, input is gathered from sensors coupled to a patient (step 24). Next, the Banzhaf power is calculated for each of the signals in the input and used to choose the top informative alarms (step 26). Next, the interdependencies of the alarms are calculated (step 28). Next, a Bayes Net is used to classify the alarms into false or true alarms (step 30). Finally, an alarm is transmitted to a computing device (step 32).

For the non-limiting purposes of this disclosure, an example of the process illustrated in FIG. 2 will be discussed in the following paragraphs to indicate the advantages of utilizing the Banzhof power in the analysis. In this example, the Physionet Challenge 2015 database was used as previously described. This database was produced by four hospitals in the United States and Europe, using monitors with different manufacturers, unit-specific protocols, software versions and unit types. The definition of the alarms is presented in this document for asystole, extreme bradycardia, extreme tachycardia, ventricular tachycardia, ventricular tachycardia, and ventricular flutter/fibrillation. Measurement for three vital signals of ECG, PLETH, and APB was utilized where each alarm is labeled as true, false. Each alarm in the dataset was reviewed by a team of experts at least two of whom agreed that the alarm was either true or false. These alarms are assumed to be at least 5 minutes apart and are triggered 5 minutes from the beginning of each record while the onset of the events is within 10 seconds of the alarm (i.e., between 4:50 and 5:00 of the record). The resolution and frequency of each signal in the data are 12 bit and 250 Hz, respectively. In addition, each signal has been filtered by a finite impulse response (FIR) band pass (0.05 to 40 Hz) and mains notch filters. As the data is real data from actual hospitals, the signals might suffer from movement artifact, sensor disconnects, interference from pacemakers and other events.

First, the six-level wavelet decomposition was applied using Daubechies 8-tap as the pair of father and mother wavelets to signals to obtain time-frequency information at different resolutions. As each sample includes 3 signals, it was represented by 18 vectors of wavelet coefficients using six levels. Subsequently, 20 statistical and information-theoretic features are extracted from each vector, resulting in a total of 360 features. The list of features calculated were those listed in Table 1.

As previously discussed, the coalition game based on Banzhaf power used to determine the top informative alarms evaluated the average marginal importance of each calculated feature when joining any potential coalition of features. The metric used to make the decision on which alarms are the top informative alarms is the interdependency of newly added features with the coalition members as defined previously. In order to obtain interdependency, the wavelet coefficients were first discretized. The quantization levels were obtained from the Lloyd algorithm previously mentioned, which minimizes the mean square error (MSE) between the continuous values and the quantized versions for a training dataset and a given number of quantization levels (5 quantization levels were chosen in this particular example). The quantized values were used to calculate the required mutual information which was further used to calculate the features' interdependencies. Then, a swinger index $\zeta_i^S$ for each feature $F_i$ with respect to coalition S was set to 1 if the feature is interdependent with at least half of the coalition members. The Banzhaf power for each feature $F_i$ was then calculated as the ratio of coalitions for which the feature $F_i$ is a swinger. The features were then ranked based on their Banzhaf powers and the top 20 highest ranked features by Banzhaf power were selected.

In order to evaluate the relevance of the obtained features, the data mining machine learning software marketed under the tradename WEKA (ver. 3.6 package) by the University of Waikato, New Zealand, was used and feature selection methods were applied to the extracted features resulting in a selection of a top 20 of them for each method based on Banzhaf power. In this example, the following attribute selection techniques were utilized: 1) Correlation-based Feature Subset Selection (CFS) to select a subset of features with the highest correlation with the labels and the lowest correlation with each other; 2) Chi-square method to choose a sub-set of features by evaluating their chi-squared statistic with respect to the class label; 3) the Gain ratio method which minimizes the conditional entropy of a class given the selected features; 4) the RELIEF method which evaluates the importance of a test feature set by examining the difference of Euclidean distances for randomly selected samples with the nearest samples of the same and different classes using the test feature set; 5) the support vector machine (SVM)-based ranker, in which the features are ranked by the square of their weights assigned by the SVM classifier.

For completeness of comparisons, popular sparsity was also employed, along with imposing regression methods including least absolute shrinkage and selection operator (LASSO) and logistic regression Fre. For comparison, the top 20 features with highest absolute coefficients in the model were selected. The results are also compared with a Shapely-based coalition game theoretic feature selection method outlined in the papers to Afghah et al., "A game theoretic predictive modeling approach to reduction of false alarm," 2015 *International Conference for Smart Health* (*ICSH '15*), *Lecture Notes in Computer Science, Chapter: Smart Health*, p. 118-130 (2016); and in Razi et al., "Blood loss severity predicition using game theoretic based feature selection," *IEEE-EMBS International Conferences on Biomedical and Health Informatics (BHI '14)*, p. 776-780 (2014); the disclosures of each of which are hereby incorporated entirely herein by reference. Another Shapley-based feature selection method that may be used in place of the Banzhof power or in combination with it may be that disclosed in the paper by Zaeri-Amirani et al., entitled "A feature selection method based on Shapley value to false alarm reduction in ICUs, a genetic-algorithm approach," available at arXiv.org at https://arxiv.org/abs/1804.11196, a copy of which is filed herewith as Appendix A and which is hereby incorporated entirely herein by reference.

Figure 3:
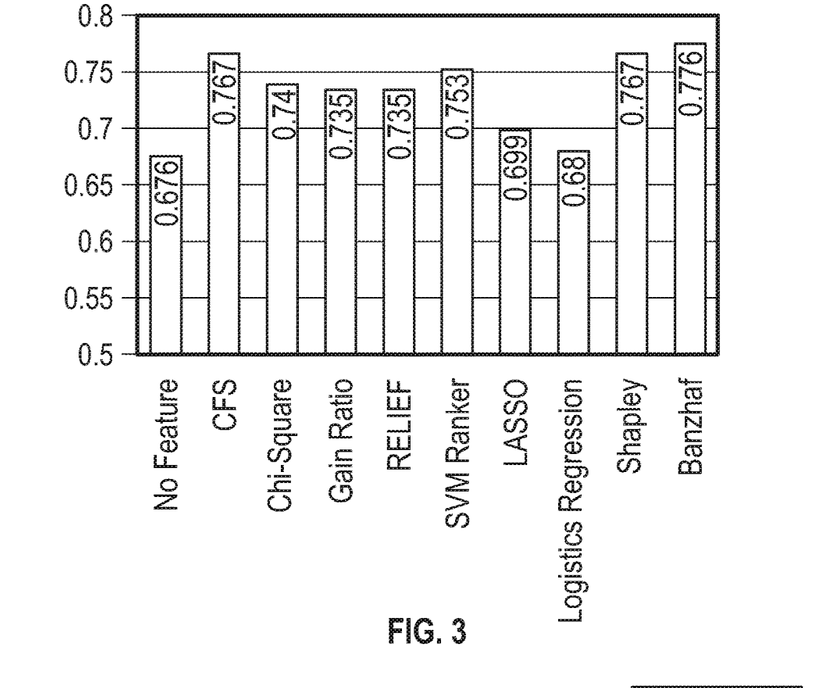
FIG. 3 is a graph that illustrates the false alarm detection rate for various feature selection methods using a Bayes-Net classification.

Referring to FIG. 3, the false alarm detection rate for various feature selection methods using a Bayes-Net classification is illustrated in a graph. In order to compare the performance of various feature selection methods, a Bayes Net with 10-fold cross validation was selected as a representative classifier to classify the alarms into false and true alarms. The proposed feature selection method (like the Banzhaf power), in various implementations, is independent of the choice of classifier technique, and it can be applied to all different classifier types techniques.

Figure 4:
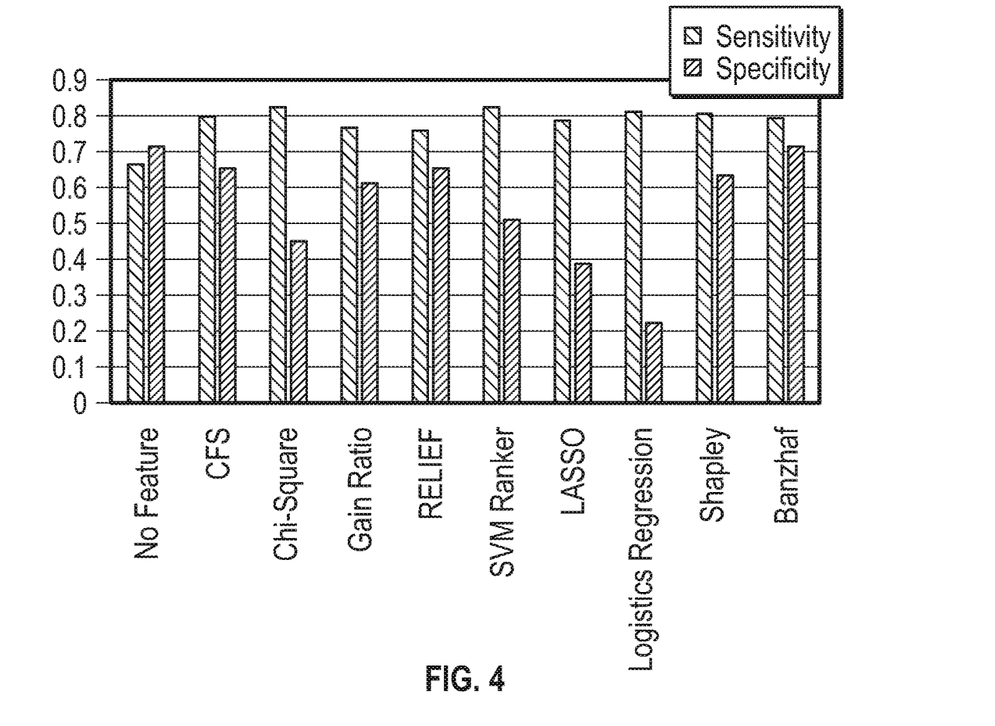
FIG. 4 is a graph that illustrates the sensitivity and specificity of various feature selection methods using a Bayes-Net classification.

Referring to FIG. 4, the sensitivity and specificity of various feature selection methods using a Bayes-Net classification is illustrated in a graph. Sensitivity is calculated as the ratio of recognized true alarms to the number of all true alarms. Likewise, specificity is calculated as the ratio of recognized false alarms to the number of all false alarms. In other words, a higher sensitivity is desired for not missing a true alarm and an acceptable level of specificity is required not to report a false alarm. The trained classifier using the Banzhaf power selected features shows a better sensitivity compared to a majority of classifiers trained using the other feature selection methods. The better sensitivity is desired because missing a true alarm may have significant consequences.

The results in FIGS. 3 and 4 show that the Banzhaf power feature selection method outperforms a majority of other feature selection methods in recognizing true and false alarms while having a low computation complexity. Unexpectedly, the false alarm recognition rate (specificity) is substantially improved compared to the best competing methods, while the true alarm recognition (sensitivity) remains almost at the same level. The low success rate for no feature selection (NoFS) is somewhat expected and demonstrates the value of feature selection, since incorporating all features in classification not only increases the time and computational load of the classifier, but also decreases the classification accuracy due to the well-known over-fitting to the dataset problem. It is also observed that the Banzhaf power feature selection method provides a similar level of accuracy compared to the feature selection method using Shapely value. However, the Banzhaf-based coalition game includes much less computational power. In the Shapely-based coalition game, the marginal importance of a feature $F_i$ when joining a coalition S with |S| members is calculated by checking all 2181 permutations. However, in the Banzhaf-based coalition game, in order to evaluate marginal importance of a feature $F_i$ with respect to coalition S, the interdependency of this feature was examined with |S| members, a process that requires much less calculations.

In places where the description above refers to particular implementations of a false alarm reduction systems and related methods and implementing components, sub-components, methods and sub-methods, it should be readily apparent that a number of modifications may be made without departing from the spirit thereof and that these implementations, implementing components, sub-components, methods and sub-methods may be applied to other false alarm reduction systems and related methods.

What is claimed is:

1. A system for determining the relevancy of a plurality of alarms, the system comprising:
   a plurality of sensors configured to be coupled to a patient, wherein the plurality of sensors is configured to gather physiological data;
   a medical monitoring device coupled to the plurality of sensors through a telecommunication channel, wherein the medical monitoring device is configured to determine a physiological state of the patient using the physiological data, wherein the medical monitoring device is further configured to issue a plurality of alarm states; and
   a processing unit coupled to the medical monitoring device through a telecommunication channel, wherein the processing unit is configured to evaluate the plurality of alarm states, determine the relevancy of each alarm state of the plurality of alarm states using a coalition-based feature selection method, and issue one or more alarms corresponding with each relevant alarm state to a computing device associated with a user;
   wherein the coalition-based feature selection method includes a Banzhaf power and classifies a one or more chosen top informative alarms from the plurality of top informative alarms into false alarms and true alarms using a Bayes-Net classifier using the processing unit; and
   wherein choosing the plurality of top informative alarms comprises determining a most informative subset of alarm states from among the plurality of alarm states, wherein determining further comprises establishing a relevance of the subset of alarm states to a target user and determining an interdependence among the subset of alarm states.

2. The system of claim 1, wherein the physiological data comprises one of electrocardiographic data, arterial blood pressure data, plethysmographic data, or any combination thereof.

3. The system of claim 1, wherein the sensors comprise one of an electrocardiogram sensor, an arterial blood pressure sensor, or a pulse oximeter.

4. The system of claim 1, wherein the plurality of alarm states comprises one of an alarm for asystole, an alarm for bradycardia, an alarm for tachycardia, an alarm for ventricular tachycardia, an alarm for ventricular fibrillation, and any combination thereof.

5. The system of claim 1, wherein the relevancy of the one or more alarm states is a true state or a false state.

6. The system of claim 1, wherein the Banzhaf power is defined as:

$$n_i(v) = \frac{1}{2^{n-1}} \sum_{S \subseteq N_1} s_i^S,$$

wherein:

$$\frac{1}{2^{n-1}}$$

represents the fraction of times that an alarm state from among the plurality of alarm states has a critical role; and $\Sigma_{S \subset N_1} \xi_i^S$ represents the impact of an alarm state from among the plurality of alarm states on each other alarm state ($F_i$) from among the plurality of alarm states where $$\zeta_i = \begin{cases} 1, & I(S; C \mid F_i) \geq 0, \gamma_i^S \geq \frac{|S|}{2} \\ 0, & \text{otherwise} \end{cases}.$$

7. The system of claim 1, wherein the medical monitoring device further comprises a translating component, the translating component configured to convert each of a plurality of physiological signals from each of the plurality of sensors.

8. A method for determining the relevancy of a plurality of alarms, the method comprising:
   gathering physiological data using a plurality of sensors, wherein the plurality of sensors is configured to be coupled to a patient;
   determining a physiological state of the patient using the physiological data, using a medical monitoring device coupled to the plurality of sensors through a telecommunication channel;
   using the medical monitoring device, issuing a plurality of alarm states;
   evaluating the plurality of alarm states using a processing unit, the processing unit configured to use a coalition-based feature selection method;
   determining the relevancy of each alarm state of the plurality of alarm states using the processing unit; and
   issuing one or more alarms corresponding with each relevant alarm state to a computing device associated with a user;
   wherein the coalition-based feature selection method includes a Banzhaf power and classifies a one or more chosen top informative alarms from the plurality of top informative alarms into false alarms and true alarms using a Bayes-Net classifier using the processing unit; and
   wherein choosing the plurality of top informative alarms comprises determining a most informative subset of alarm states from among the plurality of alarm states, wherein determining further comprises establishing a relevance of the subset of alarm states to a target user and determining an interdependence among the subset of alarm states.

9. The method of claim 8, wherein the issuing one or more alarms further comprises issuing the one or more alarms to the computing device only after the relevancy of each alarm state from among the plurality of alarm states is determined to be true.

10. The method of claim 8, wherein the determining the physiological state of the patient further comprises translating each of a plurality of physiological signals from each of the plurality of sensors using a translating component on the medical monitoring device.

11. The method of claim 8, wherein the determining the relevancy of each alarm state of the plurality of alarm states further comprises choosing a plurality of top informative alarms from among the plurality of alarm states using a Banzhaf power and the processing unit.

12. The method of claim 11, wherein choosing the plurality of top informative alarms from among the plurality of alarm states using the Banzhaf power comprises using the Banzhaf power defined as:

$$n_i(v) = \frac{1}{2^{n-1}} \sum_{S \subset N_1} \varsigma_i^S,$$

wherein:

$$\frac{1}{2^{n-1}}$$

represents the fraction of times that an alarm state from among the plurality of alarm states has a critical role; and $\Sigma_{S \subset N_1} \xi_i^S$ represents the impact of an alarm state from among the plurality of alarm states ($F_i$) from among the plurality of alarm states where $$\zeta_i = \begin{cases} 1, & I(S; C \mid F_i) \geq 0, \gamma_i^S \geq \frac{|S|}{2} \\ 0, & \text{otherwise} \end{cases}.$$

13. The method of claim 8, wherein the determining the relevancy of each alarm state of the plurality of alarm states further comprises classifying a one or more chosen top informative alarms from a plurality of top informative alarms of the plurality of alarm states into false alarms and true alarms using a Bayes-Net classifier using the processing unit.

14. The method of claim 8, wherein the issuing one or more alarms corresponding with each relevant alarm state further comprises issuing an alarm to a desktop computing device or mobile computing device.

15. The method of claim 8, wherein issuing a plurality of alarm states further comprises issuing one of an alarm for asystole, an alarm for bradycardia, an alarm for tachycardia, an alarm for ventricular tachycardia, an alarm for ventricular fibrillation, and any combination thereof.

16. A method for issuing an alarm regarding a physiological state of a patient, the method comprising:
   receiving a plurality of alarm states from a medical monitoring device at a processing unit through a telecommunication channel;
   choosing a plurality of top informative alarms using a Banzhaf power and the processing unit;
   classifying a one or more chosen top informative alarms from the plurality of top informative alarms into false alarms and true alarms using a Bayes-Net classifier using the processing unit; and
   issuing at least one alarm to a computing device associated with a user if any one or more chosen top informative alarms is classified as true;
   wherein choosing the plurality of top informative alarms further comprises determining a most informative subset of alarm states from among the plurality of alarm states, wherein determining further comprises establishing a relevance of the subset of alarm states to a target user and determining an interdependence among the subset of alarm states.

17. The method of claim 16, further comprising calculating interdependencies of the plurality of top informative alarms using the processing unit.

18. The method of claim 16, wherein choosing the plurality of top informative alarms using the Banzhaf power comprises using the Banzhaf power defined as:

$$n_i(v) = \frac{1}{2^{n-1}} \sum_{S \subset N_1} \varsigma_i^S,$$

wherein:

$$\frac{1}{2^{n-1}}$$

represents the fraction of times that an alarm state from among the plurality of alarm states has a critical role; and $\Sigma_{S \subset N_1} \xi_i^S$ represents the impact of an alarm state from among the plurality of alarm states ($F_i$) from among the plurality of alarm states where $$\zeta_i = \begin{cases} 1, & I(S; C \mid F_i) \geq 0, \gamma_i^S \geq \frac{|S|}{2} \\ 0, & \text{otherwise} \end{cases}.$$

\* \* \* \* \*

UNITED STATES PATENT AND TRADEMARK OFFICE
CERTIFICATE OF CORRECTION

PATENT NO. : 10,650,667 B1
APPLICATION NO. : 16/195585
DATED : May 12, 2020
INVENTOR(S) : Afghah et al.

It is certified that error appears in the above-identified patent and that said Letters Patent is hereby corrected as shown below:

In the Specification

Column 4, Line 7, delete "represents the traction of times", insert --represents the fraction of times--

Column 6, Line 49, delete "where $\psi(t)= \sqrt{2} \sum_{k}(-1)^{k} h_{2N-1-k} \times \varnothing (2-1).$ ", insert --where $\psi(t)= \sqrt{2} \sum_{k}(-1)^{k} h_{2N-1-k} \times \varnothing (2t-1).$ --

Column 9, Line 38, delete "of feature Fi, (FiS) is", insert --of feature Fi, (Fi $\in$ S) is--

Column 9, Line 56, delete "excluding Fi, {S : S ⊂ N, FiS}. Feature", insert --excluding Fi, {S : S ⊂ N, Fi ∉ S}. Feature--

Signed and Sealed this
Thirtieth Day of June, 2020

Andrei Iancu
*Director of the United States Patent and Trademark Office*